United States Patent
Speck et al.

(10) Patent No.: US 6,638,913 B1
(45) Date of Patent: Oct. 28, 2003

(54) CONCENTRATED INJECTION AND INFUSION SOLUTION FOR INTRAVENOUS ADMINISTRATION

(75) Inventors: Ulrich Speck, Berlin (DE); Gabriele Schuhmann-Giampieri, Berlin (DE); Peter Muschick, Ladeburg (DE); Werner Krause, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/504,108

(22) Filed: Feb. 14, 2000

Related U.S. Application Data

(62) Division of application No. 09/117,115, filed as application No. PCT/DE97/00170 on Jan. 27, 1997, now abandoned.
(60) Provisional application No. 60/012,497, filed on Feb. 29, 1996, now abandoned.

(51) Int. Cl.[7] .................. A01N 43/04; A01N 61/20; A61K 39/395; A61K 39/00
(52) U.S. Cl. ................ 514/23; 514/1; 514/44; 514/2; 530/300; 530/350; 536/22.1; 424/130.1; 424/184.1
(58) Field of Search ................. 514/1, 21, 44, 514/23; 530/300, 350; 536/22.1; 424/130.1, 184.1

(56) References Cited

FOREIGN PATENT DOCUMENTS

| EP | 0260811 | | 3/1988 |
|---|---|---|---|
| EP | 0437662 A1 | | 7/1991 |
| FR | 2435253 | | 7/1979 |
| WO | WO 89/09614 | | 10/1989 |
| WO | WO90/11094 | * | 10/1990 |
| WO | 91/13636 | | 9/1991 |
| WO | 94/14478 | | 7/1994 |
| WO | WO 94/14478 | * | 7/1994 |

* cited by examiner

Primary Examiner—Jezia Riley
(74) Attorney, Agent, or Firm—Millen, White, Zelano & Branigan, P.C.

(57) ABSTRACT

Additives to concentrated injection and infusion solutions that avoid or mitigate acute or delayed hypersensitivity reactions as well as injection and infusion solutions that contain these additives are described.

19 Claims, No Drawings

CONCENTRATED INJECTION AND INFUSION SOLUTION FOR INTRAVENOUS ADMINISTRATION

This application is a continuation of Ser. No, 09/117,115, filed Sept. 22, 1998, now abandoned. It also claims benefit of the filing date of provisional application Ser. No. 60/012, 497, filed Feb. 29, 1996, now abandoned which is a 371 of PCT/DE97/00170 filed Jan. 27, 1997. Both of these documents are incorporated by reference herein in their entirety.

SUBJECT OF THE INVENTION

The invention relates to the subjects that are characterized in the claims, i.e., the use of additives to concentrated injection and infusion solutions to mitigate delayed hypersensitivity reactions, as well as injection and infusion solutions that contain these additives.

BACKGROUND OF THE INVENTION

For some therapeutic and diagnostic medical applications, fairly large volumes of concentrated and/or viscous solutions are administered intravascularly. Examples mainly include infusions for administering large amounts of nutrients, substances with an osmotic or colloid-osmotic action, and contrast media. Typically, these solutions are administered at a ratio of 0.5–20 ml/kg of body weight; the solutions contain active ingredients and adjuvants in amounts of 10 or more % by weight and are often more viscous than the blood. These are in part also lower-concentrated, lower-dosed emulsions, suspensions or preparations of complex structures such as micelles or liposomes. The solutions formerly caused a considerable number of different side-effects, among which acute reactions were of most concern. Such effects related to direct metabolic or toxic effects of the substances administered, effects caused to some extent by extremely high and unphysiologic osmolality on the part of solutions, and unphysiologic and harmful solvents, stabilizers and buffers. In addition, acute allergic or allergy-like events occurred. Most of these undesirable effects have now been recognized as regards their causes and have been avoided through the use of better active ingredients and preparations. As a result, the frequency and severity of side-effects have been quite substantially reduced. Studies in recent years have shown, however, that a type of side-effect that used to be rarer and in any case was less noticeable is increasingly receiving attention and causing problems. In this case, these are allergy-like or other less dose-dependent, often unexplainable immediate or delayed (i.e., hours to days) hypersensitivity reactions that occur after administration, can be manifested as reddening of the skin, hives, weals, edemas, swelling of the mucous membrane and other symptoms and can escalate—admittedly in rare cases—to severe breathing difficulties and a state of shock.

The subjects of the invention are therefore additives to highly concentrated and/or viscous solutions as well as microparticle-containing preparations for intravascular administration, which avoid acute or delayed hypersensitivity reactions or mitigate their frequency and intensity. In addition, the use of additives to active-ingredient-containing solutions for the purpose of mitigating acute or delayed hypersensitivity reactions is described.

Prior Art

Additives to injection and infusion solutions are prior art. Electrolytes, sugars, and sugar alcohols such as mannitol are used to match the osmolality of hypotonic active-ingredient solutions to the osmolality of the blood. In exceptional cases, electrolytes have also been added to the active ingredient solutions in instances where this raised the osmolality beyond that of the blood (WO 90/11094). The purpose of these additions is to improve local compatibility in cases where there is contact between the active ingredient solutions in question and blood vessels and tissues, especially in the heart. In addition, stabilizers and buffers are commonly used. X-ray contrast media have been added in some cases before heparin or another clotting inhibiting substance was added to ensure high clotting protection when blood flows back into catheters and syringes that were previously filled with contrast media [Jackson, D. M. A. and P. Dawson: Current Usage of Contrast Agents, Anticoagulant and Antiplatelet Drugs in Angiography and Angioplasty in the U.K., Clinical Radiology 50, 699–704, (1995); Miller, D. L.: Heparin in Angiography: Current Patterns of Use, Radiology 172, 1007–1011, (1989), WO 94/14478]. These mixtures are also used mainly when administration is done into arteries or for x-ray visualization of veins, where it produces a local and nonsystemic protective action of the clotting inhibitor with respect to the formation of clots. The addition of local anesthetics to x-ray contrast media to alleviate pain is rendered unnecessary by the development of less strongly hypertonic preparations. Vasodilators, prostacyclins, urea, and other substances have been used or recommended to improve microcirculation or to enhance the action of contrast media (DE 4 135 193, DE 4 446 694). Finally, therapeutically effective substances or preparations have occasionally been added to contrast medium solutions to make visible their distribution in the tissue or their flowing out into the blood vessel system. Infusion solutions have been used to dilute therapeutic agents. To date, even $Na_2Ca$ EDTA (as stabilizer, but only up to about 2 mmol), Na citrate, and tris(hydroxymethyl)-methylamine ("tris")/HCL (as a buffer, in the range of 10 to 20 mmol) and inorganic and organic bases including basic amino acids (as counterions for contrast medium acids) are commonly used as x-ray contrast medium additives. In the past 30 years, efforts have been directed more at cutting back on these additives to avoid possible undesirable physiological effects. Physiologically inorganic ions have been added to match the electrolyte environment, and papaverine and prostacyclins have been added to improve vascular visualization, local anesthesia to alleviate pain and urea to improve the visualization of kidneys and urinary passages by x-ray contrast media. A survey was published by, i.a., S. H. Kim, H. K. Lee and M. C. Han: "Incompatibility of Water-Soluble Contrast Media and Intravascular Pharmacologic Agents," An In Vitro Study, Investigative Radiology 27, 45–49, (1992). A low level of association of the x-ray contrast medium molecule in the solution to be administered was judged disadvantageous since it results in an unphysiologic increase in osmolality.

Statement of Task

The object to be achieved here has become important only in recent years. The first publications on systematic studies on delayed hypersensitivity reactions after administration of contrast media date from the mid-1980s. The frequency of these reactions obviously increased with the improvement of the acute compatibility of modern preparations. It is noteworthy that the more recent nonionic x-ray contrast media directly trigger even fewer allergy-like acute side-effects than the earlier commonly used and strongly hypertonic ionic contrast media. The increase in the frequency of delayed hypersensitivity reactions, which has led to a growing number of publications and to considerable anxiety among the users, is all the more surprising and incomprehensible. Delayed reactions are defined as those side-effects that occur only one or more hours after administration of the agent in question. To date, there is no conclusive hypothesis on the causes or the mechanism of the occurrence of the delayed reactions. It is also not clear, moreover, whether some of the acute side-effects are caused by a similar mechanism, such as the delayed reactions.

The object of the invention is therefore to make available additives to contrast media that significantly mitigate or even completely avoid acute or delayed hypersensitivity reactions.

DESCRIPTION OF THE INVENTION

The mitigation and avoidance of delayed hypersensitivity reactions are achieved by the addition of substances having physical or pharmacological effects to the otherwise largely unaltered infusion or injection solutions. The actual effective components of the solutions, for example the opacifying substances or structures, are not altered.

As additives, three groups of substances have proven suitable:

a) Substances that reduce the self-association of active ingredient molecules or active ingredient components in highly concentrated infusion solutions.

Physiologically compatible electrolytes such as NaCl, $MgCl_2$, sodium acetate, meglumine chloride, $Na_2Ca$ EDTA, etc., belong to this class of substances; also suitable are amino acids, such as glycine, leucine, lysine, asparagine and aspartic acid, phenylalanine, tryptophan and their neutral, physiologically compatible salts and amides. In addition, buffers such as tris/HCl, sodium citrate or neutral substances such as urea can fulfill said function. The concentration of additives for the purpose of disassociation of the active ingredient molecules is to be selected in such a way that a marked effect occurs in this respect, without, however, the osmolality of the solutions reaching values that are physiologically very problematical (for example, 3000 mosm/kg of $H_2O$) and without toxicologically harmful concentrations or dosages of the additives being reached or the viscosity of the solution by itself being significantly increased again by the high concentration of additives. Such a disassociating effect can be recognized from, for example, a measurable reduction in the viscosity of the solution despite the addition of one or more substances (i.e., despite the increase in the total concentration of the solution).

Especially suitable concentrations of the additives range from 1 mmol to about 2000 mmol, and the range of 5 mmol to 1000 mmol is preferred. The substances in the concentration range of up to about 30 mmol that are commonly used for buffering and stabilizing x-ray contrast media are not taken into consideration. The disassociating effect of the additives can be detected either by measuring the viscosity of the solutions, measuring osmolality, or by other known physical measuring processes.

b) Substances that increase the osmolality of the active ingredient-containing solutions.

In this case, there is no matching of hypotonic solutions to the osmolality of the blood; rather the osmolality of the infusion or injection solutions is deliberately increased beyond the isotonicity that is desired in principle. It is also not the purpose of the additives to produce, in turn, pharmacological effects; the purpose of the additives is rather to supply the body with them. Thus, for example, concentrated hypertonic nutrient solutions for the purpose of nutrient supply, electrolyte solutions for the purpose of electrolyte supply, or mannitol solutions for the purpose of triggering osmotic diuresis are not meant per se. These solutions are therefore used only in highly concentrated form to reduce volume during administration. The mitigation and avoidance of acute or delayed hypersensitivity reactions are achieved, however, by additions of osmotically active, physiologically compatible substances to isotonic infusion or injection solutions, as have basically been desired, with acceptance of a hypertonia that is basically undesirable. Suitable additives in this regard are physiologically compatible inorganic or organic salts such as NaCl, Na acetate, ethanolamine acetate, salts of amino acids, sugars such as glucose, galactose, ribose, as well as alcohols such as propanediol, glycerol, and mannitol. Preferred are additives with low molecular weight, a high volume of distribution, and fast metabolic clearance. Less preferred are substances or dosages that have a strong osmodiuretic action. To fulfill their purpose, the above-mentioned additives should increase the osmolality of the infusion or injection solutions by at least 50 mosm/kg of water over the osmolality of the blood. Preferred is an increase in the osmolality of the infusion or injection solution in the amount of at least 100 mosm/kg of water, in the case of sodium chloride at least 160 mosm/kg of water to 400 to 1500 mosm/kg of water. A number of additives that are proposed to increase osmolality have also been added to infusion or injection solutions in the past. In this case, however, the additions were done only to achieve the isotonicity of the solutions, or additives were selected in concentrations that sufficed to achieve a desirable pharmacological effect without, however, unnecessarily increasing the osmolality of the solutions. Especially the development of contrast media in recent decades was aimed at reducing osmolality to isotonicity. The idea of increasing osmolality to the range of hypertonicity by otherwise ineffective additives for the purpose of improving compatibility is novel.

c) Substances with action on immunological processes.

Those substances that influence the complementary system and the activation of the clotting system have proven especially suitable. Different substances and substance classes that are effective in this regard were described, for example, by Asghar, S. S.: Pharmacological Reviews 36, 223–244, (1984). Use of these substances, however, is not done for the purpose of systemic or local prophylaxis or therapy. A local effect during the mixing and dilution processes is achieved during and after the infusion or injection of concentrated active ingredient solutions. Only during this time and only during the dilution process are locally adequate concentrations of additives present that prevent the triggering of hypersensitivity reactions. The dosages of inhibitors of the complementary system that are administered with the active ingredient solutions are generally not sufficient to achieve longer-lasting and/or generalized protective or therapeutic effects. On the contrary, the direct addition of the substances to the infusion or injection solutions to prevent hypersensitivity reactions allows such low dosages to be selected and the administration to be limited in time to such an extent that an otherwise often undesirable limitation of immune defenses or physiological clotting processes in patients does not result. Examples of suitable additives are heparin, $\epsilon$-aminocaproic acid, lysine, arginine, ornithine, cysteine, homocysteine, peptides (for example, tryptophan-tyrosine, glutathione), polylysine, polyinosinic acid, suramin, chlorpromazine and mesoporphyrin. Some representatives thereof have already been used as additives or components of x-ray contrast media in the past. Thus, it is known that heparin can be added via catheter to x-ray contrast media for the visualization of blood vessels to prevent the clotting of blood that may flow back into catheters and syringes. The application is useful only if extended pauses occur between individual injections. In the case of intravenous administration, a clotting-inhibiting additive has not been discussed to date, since blood is prevented from flowing back into bypass hoses and syringes in some other way. The need for this additive is itself disputed in arteriography. Also, amino acids have been used or recommended as components of x-ray contrast media. In this case, these are the basic amino acids that have been used as counterions for iodine-containing x-ray contrast medium acids. They were used in isolated cases instead of commonly used cations such as $Na^+$ or meglumine$^+$. Better compatibility relative to the other salts was also described for the lysine salt of amidotrizoic acid. The latter did not apply, however, to delayed hypersensitivity reactions.

The concentration of the additives in question in infusion and injection solutions can be selected in such a way that systemic effects are absent, are minor, or in any case are not decisive for protective action. Examples are as follows:

| | |
|---|---|
| Heparin | 0.1–50 IU/ml |
| ε-aminocaproic acid | 0.01–20 mg/ml |
| lysine-HCl | 0.1–100 mg/ml |
| polylysine | 0.01–10 mg/ml |
| mesoporphyrin | 0.01–2 mg/ml |
| glutathione | 0.1–50 mg/ml |

Of special interest is the possibility of achieving different effects at the same time with one and the same additive. Thus, tris/HCl simultaneously acts in a disassociating, osmolality-increasing manner and buffers the infusion solutions in the desired range. Several of the above-mentioned desirable effects are simultaneously achieved with ε-aminocaproic acid just as with the other amino acids. This keeps the infusion or injection solutions from being too complex in their composition. Also, preference is given to those additives that not only prevent delayed hypersensitivity reactions but simultaneously perform other useful functions in the infusion or injection solutions; in this regard, reduction of viscosity, stabilization of solutions, buffering and certain desirable additional pharmacological effects can be mentioned. A significant advantage of the additives according to the invention lies in the fact that in most cases, no additional treatment of patients is necessary. The additives that are administered with the infusion or injection solution act immediately and simultaneously with their injection, even in the case of one-time administration. The protective action is achieved at a considerably lower overall dose of the additives than the latter would be needed for separate prophylaxis or treatment of hypersensitivity reactions. Many of the additives that are effective in combination with infusion or injection solutions are administered separately in largely pharmacologically inert form; in any case by themselves they exert no noteworthy effect on the immune system but reduce only the undesirable effects of concentrated infusion and injection solutions. The above-described additives cause a mitigation in the activation of the immune system in different stages and a mitigation of undesirable pharmacological effects. It results in a reduction in the uptake of the actual active ingredient of the infusion or injection solutions by immunologically relevant cells and tissue. Finally, the acute and delayed hypersensitivity reactions described above are mitigated in frequency and extent, and the compatibility is improved overall.

EXAMPLES

The following embodiments of formulations are to explain the subject of the invention without limiting the latter thereto.

Example 1

59.803 g of iotrolan and 0.050 g of $Na_2CA$ EDTA and 0.040 g of $NaHCO_3$ and 0.876 g of NaCl are dissolved in distilled water, so that a final volume of 100 ml at 20° C. is reached. The finished solution is autoclaved in a tightly sealed infusion flask for 20 minutes at 121° C. The osmolality of the solution at 37° C. is 644 mosm/kg of $H_2O$, the density is 1.319 g/ml, and the viscosity is 6.15 mPas, in each case at 37° C.

Example 2

59.803 g of iotrolan and 0.010 g of $Na_2Ca$ EDTA and 0.040 g of $NaHCO_3$ and 2.250 g of glycine are dissolved in distilled water, so that a final volume of 100 ml at 20° C. is reached. The finished solution is autoclaved in a tightly sealed infusion flask for 20 minutes at 121° C. The osmolality of the solution at 37° C. is 724 mosm/kg of $H_2O$, the density is 1.327 g/ml, and the viscosity is 6.96 mPas, in each case at 37° C.

Example 3a 59.803 g of iotrolan and 0.010 g of $Na_2Ca$ EDTA and 0.040 g of $NaHCO_3$ and 1.800 g of urea are dissolved in distilled water, so that a final volume of 100 ml at 20° C. is reached. The finished solution is sterilized by filtration, decanted under sterile conditions into an infusion flask, and sealed under sterile conditions. The values at 37° C. are 608 mosm/kg of $H_2O$ for the osmolality of the solution, 1.319 g/ml for density, and 6.16 mPas for viscosity.

Example 3b 59.803 g of iotrolan and 0.010 g of $Na_2Ca$ EDTA and 0.040 $NaHCO_3$ and 15.600 g of urea are dissolved in distilled water, so that a final volume of 100 ml at 20° C. is reached. The finished solution is autoclaved in a tightly sealed infusion flask for 20 minutes at 121° C. The values at 37° C. are 3140 mosm/kg of $H_2O$ for the osmolality of the solution, 1.325 for density, and 5.35 mPas for viscosity.

Example 4

59.803 g of iotrolan and 0.010 g of $Na_2Ca$ EDTA and 0.121 g of tris are dissolved in distilled water, so that a final volume of 95 ml at 20° C. is reached. The pH is set at 7.2 with 1N HCl. It is filled up to 100 ml. The finished solution is autoclaved in a tightly sealed infusion flask for 20 minutes at 121° C. The values at 37° C. are 278 mosm/kg of $H_2O$ for the osmolality of the solution, 1.308 for density, and 5.69 mPas for viscosity.

Example 5

61.13 g of iodixanol and 0.010 g of $Na_2Ca$ EDTA and 0.121 g of tris and 5.405 g of galactose are dissolved in distilled water, so that a final volume of 95 ml at 20° C. is reached. The pH is set at 7.2 with 1N HCl. It is made up to 100 ml of solution. The finished solution is autoclaved in a tightly sealed infusion flask for 20 minutes at 121° C. The solution has an osmolality of 532 mosm/kg of $H_2O$ at 37° C.

Example 6

61.13 g of iodixanol and 0.010 g of $Na_2Ca$ EDTA and 0.121 g of tris and 1000 IU of heparin and 1.32 mg of ε-aminocaproic acid are dissolved in distilled water, so that a final volume of 95 ml at 20° C. is reached. The pH is set at 7.2 with 1N HCl or NaOH. It is made up to 100 ml of solution. The solution is autoclaved for 20 minutes at 121° C.

Example 7

62.344 g of iopromide and 0.010 g of Na$_2$Ca EDTA and 0.121 g of tris and 200 IU of heparin are dissolved in distilled water, so that a final volume of 95 ml at 200C. is reached. The pH is set at 7.2 with 1N HCl. It is made up to 100 ml of solution. The finished solution is autoclaved in a tightly sealed infusion flask for 20 minutes at 121° C. The solution has an osmolality of 564 mosm/kg of H$_2$O, a density of 1.318 g/ml, and a viscosity of 4.60 mPas, in each case at 37° C.

Example 8

68.346 g of iotrolan and 0.010 g of Na$_2$Ca EDTA and 0.121 g of tris and 2000 IU of heparin are dissolved in distilled water, so that a final volume of 95 ml at 20° C. is reached. The pH is set at 7.2 with 1N HCl. It is made up to 100 ml of solution. The finished solution is autoclaved in a tightly sealed infusion flask for 20 minutes at 121° C. The solution has an osmolality of 312 mosm/kg of H$_2$O, a density of 1.371 g/ml, and a viscosity of 11.6 mPas, in each case at 37° C.

Example 9

59.803 g of iotrolan and 0.010 g of Na$_2$Ca EDTA and 2.193 g of lysine are dissolved in distilled water, so that a final volume of 95 ml at 20° C. is reached. The pH is set at 7.2 with 1N HCl. It is made up to 100 ml of solution. The finished solution is autoclaved in a tightly sealed infusion flask for 20 minutes at 121° C. The solution has an osmolality of 543 mosm/kg of H$_2$O, a density of 1.315 g/ml, and a viscosity of 6.2 mPas, in each case at 37° C.

Example 10

59.803 g of iotrolan and 0.010 g of Na$_2$Ca EDTA and 1.46 g of lysine are dissolved in distilled water, so that a final volume of 95 ml at 200C. is reached. The pH is set at 7.2 with 1N HCl. It is made up to 100 ml of solution. The finished solution is autoclaved in a tightly sealed infusion flask for 20 minutes at 121° C. The solution has an osmolality of 445 mosm/kg of H$_2$O, a density of 1.311 g/ml, and a viscosity of 6.0 mPas, in each case at 37° C.

Example 11

59.803 g of iotrolan and 0.010 g of Na$_2$Ca EDTA and 3.07 g of glutathione are dissolved in distilled water, so that a final volume of 95 ml at 20° C. is reached. The pH is set at 7.2 with 1N HCl or 1N NaOH. It is made up to 100 ml of solution. The finished solution is autoclaved in a tightly sealed infusion flask for 20 minutes at 121° C. The solution has an osmolality of 455 mosm/kg of H$_2$O, a density of 1.312 g/ml, and a viscosity of 6.2 mPas, in each case at 37° C.

Example 12

78.886 g of iopromide and 0.010 g of Na$_2$Ca EDTA and 0.292 g of lysine are dissolved in distilled water, so that a final volume of 95 ml at 20° C. is reached. The pH is set at 6.8 with 1N HCl. It is made up to 100 ml of solution. The finished solution is autoclaved in a tightly sealed infusion flask for 20 minutes at 121° C. The solution has an osmolality of 780 mosm/kg of H$_2$O, a density of 1.403 g/ml, and a viscosity of 9.7 mPas, in each case at 37° C.

Example 13

64.7 g of iohexol and 0.010 g of Na$_2$Ca EDTA and 0.121 g of tris and 5.7 mg of mesoporphyrin are dissolved in distilled water, so that a final volume of 95 ml at 20° C. is reached. The pH is set at 7.4 with 1N HCl. It is made up to 100 ml of solution. The finished solution is sterilized by filtration. The solution has an osmolality of 670 mosm/kg of H$_2$O, a density of 1.344 g/ml, and a viscosity of 5.9 mPas, in each case at 37° C.

What is claimed is:

1. A method to avoid or mitigate delayed hypersensitivity reactions following administration of an X-ray contrast agent, comprising administering to a patient a concentrated injection or infusion solution comprising a contrast agent and, as an additive, a clotting-inhibiting substance at a concentration of 0.1–50 IU/ml.

2. The method according to claim 1, wherein the clotting-inhibiting substance is heparin.

3. The method according to claim 1, wherein the contrast agent is monomeric and nonionic.

4. The method according to claim 1, wherein the contrast agent is nonionic and dimeric.

5. A method to avoid or mitigate delayed hypersensitivity reactions following administration of an X-ray agent, comprising administering to a patient a concentrated injection or infusion solution comprising a contrast agent and, as an additive, an inhibitor of complement activation at a concentration of 0.01–100 mg/ml, wherein the inhibitor of complement activation is heparin, ε-aminocaproic acid, lysine, arginine, ornithine, cysteine, homocysteine, a peptide, a polypeptide, tryptophan-tyrosine, glutathione, polylysine, polyinosinic acid, suramin, chlorpromazine or mesoporphyrin.

6. A method according to claim 5, wherein the inhibitor of complement activation is heparin.

7. A method according to claim 1, wherein the clotting-inhibiting substance is heparin, ε-aminocaproic acid, lysine, arginine, ornithine, cysteine, homocysteine, a peptide, a polypeptide, tryptophan-tyrosine, glutathione, polylysine, polyinosinic acid, suramin, chlorpromazine or mesoporphyrin.

8. A method according to claim 1, wherein said concentrated injection or infusion solution further comprises an osmolality-increasing substance at a concentration that causes an increase of osmolality in the amount of at least 100 mosm/kg of water.

9. A method according to claim 8, wherein the osmolality-increasing substance is a physiologically compatible inorganic salt, organic salt, or salt of an amino acid, sugar or alcohol.

10. A method according to claim 1, wherein said concentrated injection or infusion solution further comprises one or more amino acids, salts thereof and/or amides thereof.

11. A method according to claim 10, wherein said one or more amino acids are selected from glycine, leucine, lysine, asparagine, aspartic acid, phenylalanine and tryptophan, salts thereof and amides thereof.

12. A method according to claim 1, wherein said concentrated injection or infusion solution further comprises urea.

13. A method according to claim 5, wherein the contrast agent is monomeric and nonionic.

14. A method according to claim 5, wherein the contrast agent is nonionic and dimeric.

15. A method according to claim 5, wherein said concentrated injection or infusion solution further comprises an osmolality-increasing substance at a concentration that causes an increase of osmolality in the amount of at least 100 mosm/kg of water.

16. A method according to claim 15, wherein the osmolality-increasing substance is a physiologically compatible inorganic salt, organic salt, or salt of an amino acid, sugar or alcohol.

17. A method according to claim 5, wherein said concentrated injection or infusion solution further comprises one or more amino acids, salts thereof and/or amides thereof.

18. A method according to claim 17, wherein said one or more amino acids are selected from glycine, leucine, lysine, asparagine, aspartic acid, phenylalanine and tryptophan, salts thereof and amides thereof.

19. A method according to claim 5, wherein said concentrated injection or infusion solution further comprises urea.

* * * * *